United States Patent
Ueshima et al.

(10) Patent No.: US 8,962,682 B2
(45) Date of Patent: *Feb. 24, 2015

(54) JELLY COMPOSITION

(75) Inventors: Hiroki Ueshima, Shizuoka (JP); Shigeharu Suzuki, Shizuoka (JP); Naomi Yokomizo, Saitama (JP); Atsushi Sato, Tochigi (JP); Hirosato Fujii, Shizuoka (JP); Shigeru Kimura, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 868 days.

This patent is subject to a terminal disclaimer.

(21) Appl. No.: 12/084,643

(22) PCT Filed: Nov. 10, 2006

(86) PCT No.: PCT/JP2006/322483
§ 371 (c)(1), (2), (4) Date: May 7, 2008

(87) PCT Pub. No.: WO2007/055327
PCT Pub. Date: May 18, 2007

(65) Prior Publication Data
US 2009/0111777 A1 Apr. 30, 2009

(30) Foreign Application Priority Data

Nov. 11, 2005 (JP) .................................. 2005-327341
Feb. 17, 2006 (JP) .................................. 2006-040799

(51) Int. Cl.
*A01N 37/00* (2006.01)
*A61K 31/19* (2006.01)
*A61K 31/20* (2006.01)

(52) U.S. Cl.
USPC ........................................ 514/557; 514/560

(58) Field of Classification Search
USPC ........................................................ 514/557
See application file for complete search history.

(56) References Cited

U.S. PATENT DOCUMENTS 5,348,738 A * 9/1994 Takatsuka et al. ......... 424/78.37
5,932,235 A * 8/1999 Ninomiya et al. ............ 424/401
6,458,395 B1 10/2002 Emoto et al.
2004/0018248 A1 1/2004 Bendich
2005/0037068 A1 2/2005 Massironi
2005/0147665 A1 * 7/2005 Horrobin et al. .............. 424/456

FOREIGN PATENT DOCUMENTS

| | | |
|---|---|---|
| JP | 2-186953 A | 7/1990 |
| JP | 8-242786 A | 9/1996 |
| JP | 9-224578 A | 9/1997 |
| JP | 11-56245 A | 3/1999 |
| JP | 11-56315 A | 3/1999 |
| JP | 2001-114696 A | 4/2001 |
| JP | 2001-120197 A | 5/2001 |
| JP | 2002-153218 A | 5/2002 |
| JP | 2004-8165 A | 1/2004 |
| JP | 2004-514684 A | 5/2004 |
| JP | 2004339086 A * | 12/2004 |
| JP | 2005-82536 A | 3/2005 |
| JP | 2005-508982 A | 4/2005 |
| WO | WO-99/34690 A1 | 7/1999 |
| WO | WO-00/24424 A1 | 5/2000 |
| WO | WO 03103640 A1 * | 12/2003 |

* cited by examiner

*Primary Examiner* — Layla Soroush
(74) *Attorney, Agent, or Firm* — Birch, Stewart, Kolasch & Birch, LLP

(57) ABSTRACT

It is intended to provide a composition having at least one effect among the following effects; a plurality of medicinal ingredients can be taken as one preparation and the convenience for patients is excellent; the drug compliance is excellent; the amount of jelly composition to be taken at a time is small; the release of an active ingredient in the digestive tract is excellent; the absorption of an active ingredient to the body is excellent; the storage stability of an active ingredient is excellent; the dispersibility of an active ingredient in the composition is excellent; the storage stability of the composition is excellent; the syneresis of the composition is less, it has an appropriate jelly strength to a degree that does not disintegrate during carrying and before taking and easily disintegrates after taking; the handleability during preparation of the composition is excellent; the portability of the composition is excellent; the feeling of taking the composition is excellent; it has an effect on reducing side effects; and the like. The jelly composition contains a polyvalent unsaturated fatty acid, a second medicinal ingredient, an emulsifying agent and a gelling agent.

8 Claims, No Drawings

JELLY COMPOSITION

TECHNICAL FIELD

This invention relates to a jelly composition containing a polyunsaturated fatty acid as a pharmaceutical component together with a second pharmaceutical component, which is convenient and easy to take and which is highly stable. More specifically, this invention relates to a pharmaceutical composition.

BACKGROUND ART

A polyunsaturated fatty acid is defined as a fatty acid including two or more carbon-carbon double bonds in one molecule, and the polyunsaturated fatty acids are categorized by the position of the double bond into ω3 fatty acid, ω6 fatty acid, and the like. The ω3 polyunsaturated fatty acids include α-linolenic acid, icosapentaenoic acid (EPA), and docosahexaenoic acid (DHA), and the ω6 polyunsaturated fatty acids include linoleic acid, γ-linolenic acid, and arachidonic acid. Polyunsaturated fatty acids exhibit various actions including antiarteriosclerotic action, platelet aggregation inhibitory action, hypolipidemic action, antiinflammatory action, antitumor action, and central action, and therefore, polyunsaturated fatty acids are incorporated in various foods, or sold as a health food or pharmaceutical product. For example, ethyl icosapentaenoate (EPA-E) which is a polyunsaturated fatty acid is commercially available as a therapeutic agent for arteriosclerosis obliterans (ASO) and hyperlipidemia.

Since polyunsaturated fatty acid is susceptible to oxidation, and peculiar smell develops with the oxidation, the polyunsaturated fatty acid is generally incorporated in a capsule to thereby prevent the oxidation and seal the unpleasant smell. In the meanwhile, several hundred milligrams to several grams of polyunsaturated fatty acid should be taken at one dose to achieve the effect as described above, and this results in the problems of difficulty of taking a large capsule, difficulty of taking many capsules at a time, and the like. Such problems are particularly serious in the case of elderly patients with reduced ability of swallowing. Taking such large-size capsule and/or large-number capsules has also been highly unpleasant in the case of patients who are allowed to take only limited amount of water because they had to take the large-size capsule and/or large-number capsules with the limited amount of water. In addition, a dosage form which can be conveniently used in the administration to the so called "bedridden" patients requiring tube administration has also been demanded.

The patients who are taking the EPA-E for the hyperlipidemia often suffer from complication with other diseases, and in such a case, they are required to take two or more drugs, and a typical such case is metabolic syndrome. In the case of metabolic syndrome, patients suffer from complication of two or more of hypertension, abnormal glucose tolerance, dyslipidemia, obesity, and the like, and such multiplicity of the risk factors resulted in the higher occurrence of coronary artery diseases, cerebral infarction, and the like. Recently, this attracted public attention. In the U.S., the number of patients suffering from the metabolic syndrome is estimated to be as high as 50,000,000, and this has become a social problem. Increase in the number of patients is also feared in Japan where Westernization of the life has occurred. Treatment of the metabolic syndrome is based on the improvement of lifestyle, and more specifically, on the alimentary therapy and kinesitherapy. However, such improvement of the dietary life or the lack of exercise is often difficult in the patients suffering from the "lifestyle-related diseases", and they usually transfer to pharmacotherapy in order to prevent poor prognosis, for example, onset of myocardial infarction or cerebral infarction. As described above, metabolic syndrome simultaneously involves hypertension, abnormal glucose tolerance, and dyslipidemia, and therefore, the treatment would be based on the administration of a plurality of drugs, and the patients have to take a plurality of drugs for a long period. However, taking multiple drugs for a long period precisely as prescribed without any error or forgetting is difficult, and this is particularly true since patients of the metabolic syndrome are often elderly people including the people suffering from reduced swallowing ability. For such group of patients, dosage forms of conventional preparations such as tablet, capsule, powder, and granules have not always been easy to take.

Such patients with reduced swallowing ability often develop pneumonia from aspiration of food or beverage into the trachea. Such aspiration is known to occur less frequently in the case of a highly viscous gel or a jelly compared to liquid with low viscosity such as water (see Fujishima, I. "Eating from mouse: Q&A on dysphagia" published from Chuohoki Publishers Co., Ltd.). In view of such situation, jelly preparations have recently been developed as pharmaceutical preparations which can be easily taken by patients with low swallowing ability. Exemplary such commercially available jelly preparations include Acivir Oral Jelly (manufactured by Teikoku Medix Co., Ltd. and sold by Nikken Chemical) having acyclovir (an antiviral drug) incorporated therein, Ciloslet Oral Jelly (manufactured by Teikoku Medix Co., Ltd. and sold by Zeria Pharmaceutical Co., Ltd.) having cilostazol (a therapeutic agent for chronic artery obstruction) incorporated therein, and Pabron Cough Medicine <Stick Jelly> (manufactured by Teikoku Medix Co., Ltd. and sold by Taisho Pharmaceutical Co., Ltd.) which is an over-the-counter drug.

Jelly preparations are known in the art, and examples include the jelly composition having incorporated therein carageenan, locust bean gum, xanthan gum, and phosphate buffer solution together with Chinese medicine bulk (see, for example, Patent Document 1), and a jelly composition having incorporated therein carageenan, carob bean gum, poly(sodium acrylate), and a surfactant together with cilostazol (antiplatelet drug) (see, for example, Patent Document 2). However, a jelly composition containing a polyunsaturated fatty acid and a second pharmaceutical component is neither disclosed nor suggested in such known jelly compositions having a pharmaceutical component incorporated therein.

A drug containing a transmucosal absorbefacient comprising a polyunsaturated fatty acid and a polymer gel is also disclosed (see, for example, Patent Document 3). In this document, however, the polyunsaturated fatty acid and the macromolecule gel are used as an aid (transmucosal absorbefacient) for facilitating absorption of a substance that is not readily absorbed from the digestive tract (for example, insulin) from the mucosa, for example, by rectal administration, and the pharmaceutical and pharmacological action of the polyunsaturated fatty acid itself is neither disclosed nor suggested.

As a preparation containing a second pharmaceutical component together with the polyunsaturated fatty acid, a tablet containing DHA with simvastatin and vitamins has been disclosed (see for example, Patent Document 4). Also disclosed is a method for incorporating a liquid active component in a solid pharmaceutical composition (see for example, Patent Document 5). This document discloses a sachet having a mixture of ω3 triglyceride and simvastatin filled therein.

However, none of these prior art documents disclosing the combination of the polyunsaturated fatty acid and a second pharmaceutical component teach or suggest the jelly composition.

[Patent Document 1] JP 2001-114696 A
[Patent Document 2] JP 2005-82536 A
[Patent Document 3] JP 2000-128805 A
[Patent Document 4] JP 2004-514684 A
[Patent Document 5] JP 2005-508982 A

DISCLOSURE OF THE INVENTION

Problems to be Solved by the Invention

An object of the present invention is to provide a jelly composition, and in particular, a pharmaceutical composition containing a polyunsaturated fatty acid which is a pharmaceutical component together with a second pharmaceutical component, which has at least one of the following characteristic features: high convenience for the patient since two or more pharmaceutical components can be taken at a time which also results in high administration compliance; reduced amount of the jelly composition that needs to be taken at a time; improved release of the effective components in the digestive tract; improved absorption of the effective components into the body; improved storage stability of the effective components; improved dispersibility of the effective components in the composition; improved storage stability of the composition; reduced syneresis of the composition; adequate jelly strength so that the composition does not disintegrate during the transportation or before taking but easily disintegrates once taken; handling convenience in the preparation of the composition; portability of the composition; gratification in taking the composition; and effect of reducing the side effects.

Means for Solving the Problems

In order to solve the problems as described above, the present invention provides a jelly composition comprising a polyunsaturated fatty acid as a first pharmaceutical component; a second pharmaceutical component; an emulsifier; and a gelling agent.

Effect of the Invention

The jelly composition of the present invention contains a polyunsaturated fatty acid which is a pharmaceutical component together with a second pharmaceutical component. This composition is a composition having at least one of the following characteristic features: high convenience for the patient since two or more pharmaceutical components can be taken at a time which also results in high administration compliance; reduced amount of the jelly composition that needs to be taken at a time; improved release of the effective components in the digestive tract; improved absorption of the effective components into the body; improved storage stability of the effective components; improved dispersibility of the effective components in the composition; improved storage stability of the composition; reduced syneresis of the composition; adequate jelly strength so that the composition does not disintegrate during the transportation or before taking but easily disintegrates once taken; handling convenience in the preparation of the composition; portability of the composition; gratification in taking the composition; and effect of reducing the side effects; and more particularly, an orally administered pharmaceutical composition which has such characteristic features.

BEST MODE FOR CARRYING OUT THE INVENTION

Next, the present invention is described in detail.

A polyunsaturated fatty acid is defined as a fatty acid having two or more carbon-carbon double bonds in the molecule, and the polyunsaturated fatty acids are further grouped by the position of the double bond into $\omega$-3, $\omega$-6, and other polyunsaturated fatty acids. Exemplary $\omega$-3 polyunsaturated fatty acids include $\alpha$-linolenic acid, EPA, and DHA, and exemplary $\omega$-6 polyunsaturated fatty acids include linoleic acid, $\gamma$-linolenic acid, and arachidonic acid. The polyunsaturated fatty acid used in the present invention may be either a synthetic or a natural polyunsaturated fatty acid, or a natural oil containing such polyunsaturated fatty acids. Synthetic products include those which have been produced by chemical synthesis, and semi-synthetic products which have been produced by microorganisms and then subjected to esterification, ester exchange, or the like. The natural products may be either those extracted from a natural oil containing polyunsaturated fatty acids by a known means or those which have been further processed to produce crude products or further purified products. Salts of a polyunsaturated fatty acid as well as derivatives such as ester, amide, phospholipid, monoglyceride, diglyceride, and triglyceride of a polyunsaturated fatty acid are also included within the polyunsaturated fatty acid used in the present invention.

The polyunsaturated fatty acid used in the present invention is preferably an $\omega$3 polyunsaturated fatty acid, and more preferably, the polyunsaturated fatty acid is at least one member selected from EPA, DHA, and $\alpha$-linolenic acid. Still more preferably, the polyunsaturated fatty acid is EPA, DHA, or a mixture thereof, and even more preferably, the polyunsaturated fatty acid is ethyl icosapentate (EPA-E), ethyl docosahexaenoate (DHA-E), or a mixture thereof. Most preferably, the polyunsaturated fatty acid is EPA-E. An example of the mixture of EPA-E and DHA-E is Omacor (a soft capsule containing about 46% by weight of EPA-E and about 38% by weight of DHA-E manufactured by Ross Products), which is commercially available in the U.S. and the like as a therapeutic agent for hypertriglyceridemia, and which may be used in the present invention. The compositional ratio of the EPA-E/DHA-E is not particularly limited as long as the merits of the present invention are realized. Also preferred are the embodiments wherein the polyunsaturated fatty acid is in the form of a purified fish oil as well as the embodiments wherein the polyunsaturated fatty acid is at least one member selected from monoglyceride, diglyceride, and triglyceride.

The purity of the polyunsaturated fatty acid used in the composition of the present invention, namely, content of the polyunsaturated fatty acid in the entire fatty acid is not particularly limited. However, the purity is preferably at least 25% by weight, more preferably at least 50% by weight, still more preferably at least 70% by weight, and even more preferably at least 85% by weight, and most preferably, the purity of the polyunsaturated fatty acid is such that it is substantially free from fatty acid components other than the polyunsaturated fatty acid. It is to be noted that the "fatty acid" referred in the passage "substantially free from fatty acid components other than the polyunsaturated fatty acid" only designates the fatty acid that functions as an effective component, and fatty acid incorporated, for example, as an emulsifier is not included in the "other fatty acid components".

The amount of the polyunsaturated fatty acid used in the present invention is not particularly limited as long as the merits of the present invention are retained. However, the polyunsaturated fatty acid is preferably used in an amount of 10 to 50% by weight, and more preferably, in 15 to 30% by weight in relation to the total amount of the jelly composition, and this amount is adequately determined by considering amount of the jelly composition filled in the container, purity of the polyunsaturated fatty acid, and the like.

For example, when the jelly contains 20% by weight of the polyunsaturated fatty acid, 600 mg of the polyunsaturated fatty acid can be taken by taking 3 g of the jelly. In order to enable efficient absorption of the polyunsaturated fatty acid in the body, the polyunsaturated fatty acid should be taken after the meal. In such a case, the patient is already feeling full, and amount of the jelly that should be taken is an important factor in the compliance. The amount of the jelly should also be reduced in the case of elderly people with less ability of swallowing as well as in the case of patients who are allowed to take only limited amount of water. Accordingly, industrial value will be improved if oil content in the jelly can be increased.

The second pharmaceutical component in the composition of the present invention is not particularly limited. However, examples include drugs for central nervous system such as hypnotic sedative drugs, antianxiety drugs, antiepileptic drugs, antipyretic analgesic antiphlogistic drugs, stimulating drugs, psychostimulants, antiparkinsonian drugs, drugs for psychoneurosis, cold remedies, dementia drugs, and other drugs for central nervous system; drugs for peripheral nervous system such as topical anesthetics, skeletal muscle relaxants, drugs for autonomic nerve, and antispastics; drugs for sensory organs such as ophthalmic drugs, otolaryngologic drugs, and drugs for vertigo; drugs for circulatory organs such as cardiotonics, arrhythmia drugs, diuretic drugs, hypotensive agents, vasoconstrictors, vasodilators, antihyperlipidemic agents, and other drugs for circulatory organ; drugs for respiratory organs such as antitussive drugs, expectorants, antitussive expectorants, and bronchodilators; drugs for digestive organs such as antidiarrheal drugs, drugs for controlling intestinal function, peptic ulcer drugs, stomachics digestives, antacids, cathartics, cholagogues, and other drugs for digestive organs; hormone drugs (including antihormone drugs) such as salivary gland hormone drugs, thyroid hormone drugs, parathyroid hormone drugs, anabolic steroids, adrenal hormone drugs, androgen drugs, estrogens, mixed hormone drugs, and other hormone drugs (including the antihormone drugs); drugs for urogenital organ and anus such as drugs for excretory organ, oxytocics, haemorrhoid drugs, and other drugs for urogenital organ and anus; renal disease drugs; drugs for other individual organ systems; vitamin drugs such as vitamin A and D drugs, vitamin B1 drugs, vitamin B drugs, vitamin C drugs, vitamin E drugs, vitamin K drugs, mixed vitamin drugs, and other vitamin drugs; analeptics such as calcium drugs, mineral drugs, sugar drugs, protein amino acid drugs, organ preparations, analeptics for infants, and other analeptics; drugs for blood and body fluids such as blood anticoagulants, antiplatelet drugs, and other drugs for blood and body fluids; metabolic drugs such as drugs for liver diseases, antidotes, drugs for addictive intoxication, gout drugs, enzyme drugs, antidiabetic agents, glucose tolerance improving agents, and other metabolic drugs; cell activating drugs; drugs for tumors such as alkylating agents, antimetabolites, antitumor antibiotics, antitumor vegetative drugs, and other tumor drugs; radiopharmaceuticals; antiallergic drugs such as antihistaminic agents, drugs for irritation therapy, and other antiallergic drugs; drugs based on the formulation of herbal medicine and Chinese medicine; antibiotic pharmaceuticals such as antibiotic pharmaceuticals which mainly acts on Gram-positive bacteria, antibiotic pharmaceuticals which mainly acts on Gram-negative bacteria, antibiotic pharmaceuticals which mainly acts on Gram-positive and negative bacteria, antibiotic pharmaceuticals which mainly acts on Gram-positive bacteria and mycoplasma, antibiotic pharmaceuticals which mainly acts on Gram-positive and negative bacteria, rickettsia, and chlamydia, antibiotic pharmaceuticals which mainly acts on acidophilic bacteria, antibiotic pharmaceuticals which mainly acts on mold, and other antibiotic pharmaceuticals (including mixed antibiotic pharmaceuticals); chemotherapeutic drugs such as sulfa drugs, antituberculous drugs, antileprosy drugs, synthetic antibacterial drugs, antiviral drugs, and other chemotherapeutic drugs; drugs for zooparasites such as antiprotozoals and anthelmintics; alkaloid narcotics (natural narcotics) such as opium alkaloid narcotics and coca alkaloid narcotics; and non-alkaloid narcotics such as synthetic narcotics. Among these, the preferred are antihyperlipidemic agents, hypotensive agents, vasodilators, antidiabetic agents or glucose tolerance improving agents, antiplatelet drugs, dementia drugs, antiviral drugs, cholagogues, renal disease drugs, drugs for central nervous system, thyroid hormone drugs, vitamin E drugs, and pharmaceuticals based on herbal medicine and Chinese medicine, and the most preferred are antihyperlipidemic agents.

Exemplary antihyperlipidemic agents include statin drugs (HMG-COA reductase inhibitors) such as pravastatin, simvastatin, lovastatin, fluvastatin, atorvastatin, cerivastatin, pitavastatin, and rosuvastatin; fibrates such as bezafibrate and fenofibrate; squalene synthase inhibitor (such as TAK-475); and cholesterol absorption inhibitor (such as ezetimibe). The preferred are statin drugs such as pravastatin, simvastatin, fluvastatin, atorvastatin, pitavastatin, and rosuvastatin.

Exemplary hypotensive agents and vasodilators include angiotensin II receptor antagonists such as candesartan, losartan, valsartan, telmisartan, and olmesartan; angiotensin converting enzyme inhibitors such as enalapril, alacepril, imidapril, quinapril, temocapril, delapril, benazepril, captopril, cilazapril, trandolapril, perindopril, and lisinopril; calcium antagonists such as amlodipine, cilnidipine, nifedipine, nicardipine, azelnidipine, efonidipine, barnidipine, manidipine, nilvadipine, felodipine, benidipine, nisoldipine, and nitrendipine; α1 blockers such as doxazosin, bunazosin, and prazosin; β blockers; and diuretic drugs. The preferred are angiotensin II receptor antagonists, angiotensin converting enzyme inhibitors, calcium antagonists, and/or α1 blockers such as candesartan, losartan, valsartan, olmesartan, enalapril, amlodipine, cilnidipine, nifedipine, and/or doxazosin.

Exemplary antidiabetic agents or glucose tolerance improving agents include a glucosidase inhibitors such as voglibose and acarbose; biguanide drugs such as metformin and buformin; thiazolidine drugs such as pioglitazone, rosiglitazone, and rivoglitazone; sulfonyl urea drugs such as glimepiride, glibenclamide, and gliclazide; and short acting insulin secretagogues such as mitiglinide and nateglinide. The preferred are a glucosidase inhibitors, biguanide drugs, thiazolidine drugs, and/or short acting insulin secretagogues such as voglibose, metformin, pioglitazone, rosiglitazone, rivoglitazone, mitiglinide, and/or nateglinide.

Exemplary antiplatelet drugs include ADP receptor antagonists such as aspirin and ticlopidine; PDE inhibitors such as cilostazol; sarpogrelate; and clopidogrel.

Exemplary dementia drugs include donepezil, and exemplary antiviral drugs include ribabirin. Exemplary cholagogues include ursodeoxycholic acid, and exemplary renal disease drugs include dilazep and dipyridamole. Exemplary drugs for central nervous system include perphenazine and sulpiride, and exemplary thyroid hormone drugs include levothyroxine. Exemplary vitamin E drugs include tocopherol acetate, and drugs based on herbal medicine or Chinese medicine include gosha-jinki-gan extract and hachimijiogan extract.

It is to be noted that the second pharmaceutical component is not limited to a single component, and the second pharmaceutical component may include two or more components showing the same drug efficacy, two or more components showing the different drug efficacies, or a combination thereof.

Exemplary preferable combinations of the second pharmaceutical component include two or more drugs respectively selected from antihyperlipidemic agent, hypotensive agent, and vasodilator; and antidiabetic agent and glucose tolerance improving agent. More specifically, exemplary combinations include the combination of a statin drug and an angiotensin II receptor antagonist; and a combination of a statin drug and a calcium antagonist.

The second pharmaceutical component may be either a commercially available component or a component synthesized by any of the methods commonly used in the art. Alternatively, the second pharmaceutical component may be the one prepared by pulverizing a commercially available drug, content of a commercially available capsule with no further processing, or an extract of such pulverized drug or capsule content.

Content of the second pharmaceutical component in one package of the jelly composition is not particularly limited. However, the second pharmaceutical component is preferably incorporated at 1/10 to 2 times the daily dose, more preferably, at 1/3 to the daily dose, and more preferably, at the daily dose. When synergistic effect is expected for the combination, the amount should be adequately reduced. For example, in the case of a statin drug, the typical content is 1 to 60 mg, and more specifically, 5 to 20 mg in the case of pravastatin, 5 to 20 mg in the case of simvastatin, 20 to 60 mg in the case of fluvastatin, 5 to 40 mg in the case of atorvastatin, 1 to 4 mg in the case of pitavastatin, and 2.5 to 20 mg in the case of rosuvastatin. In the case of a cholesterol absorption inhibitor, the typical content is 5 to 20 mg in the case of ezetimibe. In the case of an angiotensin II receptor antagonist, the typical content is 2 to 160 mg, and more specifically, 2 to 12 mg in the case of candesartan, 25 to 100 mg in the case of losartan, 40 to 160 mg in the case of valsartan, and 5 to 40 mg in the case of olmesartan. In the case of an angiotensin converting enzyme inhibitor, the typical content is 0.25 to 150 mg, and more specifically, 2.5 to 10 mg in the case of enalapril, and in the case of a calcium antagonist, the typical content is 2 to 60 mg, and more specifically, 2.5 to 5 mg in the case of amlodipine, 5 to 20 mg in the case of cilnidipine, and 10 to 40 mg in the case of nifedipine. In the case of an α1 blocker, the typical content is 0.3 to 12 mg, and more specifically, 0.5 to 8 mg in the case of doxazosin, and in the case of an α glucosidase inhibitor, the typical content is 0.2 to 300 mg, and more specifically, 0.2 to 0.9 mg in the case of voglibose. In the case of a biguanide drug, the typical content is 30 to 750 mg, and more specifically, 150 to 750 mg in the case of metformin, and in the case of a thiazolidine drug, the typical content is 1 to 45 mg, and more specifically, 15 to 45 mg in the case of pioglitazone, and 2 to 8 mg in the case of rosiglitazone. In the case of a short acting insulin secretagogue, the typical content is 10 to 360 mg, and more specifically, 10 to 30 mg in the case of mitiglinide, and 90 to 360 mg in the case of nateglinide. In the case of a dementia drug, the typical content is 3 to 5 mg in the case of donepezil.

Exemplary preferable combinations of the polyunsaturated fatty acid (the first pharmaceutical component) and the second pharmaceutical component include: EPA-E and an antihyperlipidemic agent; EPA-E and a statin drug; EPA-E and a hypotensive agent or a vasodilator; EPA-E and an angiotensin II receptor antagonist; EPA-E and a calcium antagonist; EPA-E and an antidiabetic agent or a glucose tolerance improving agent; EPA-E, a statin drug, and a hypotensive agent or a vasodilator; EPA-E, a statin drug, and an antidiabetic agent or a glucose tolerance improving agent; EPA-E, a statin drug, a hypotensive agent or a vasodilator, and an antidiabetic agent or a glucose tolerance improving agent; EPA-E and a dementia drug; a mixture of EPA-E and DHA-E and an antihyperlipidemic agent; a mixture of EPA-E and DHA-E and a statin drug; a mixture of EPA-E and DHA-E and a hypotensive agent or a vasodilator; a mixture of EPA-E and DHA-E and an angiotensin II receptor antagonist; a mixture of EPA-E and DHA-E and a calcium antagonist; a mixture of EPA-E and DHA-E and an antidiabetic agent or a glucose tolerance improving agent; a mixture of EPA-E and DHA-E, a statin drug, and a hypotensive agent or a vasodilator; a mixture of EPA-E and DHA-E, a statin drug, and an antidiabetic agent or a glucose tolerance improving agent; a mixture of EPA-E and DHA-E, a statin drug, a hypotensive agent or a vasodilator, and an antidiabetic agent or a glucose tolerance improving agent; and a mixture of EPA-E and DHA-E and a dementia drug.

Examples of the preferable combination and the preferable contents of the polyunsaturated fatty acid (the first pharmaceutical component) and the second pharmaceutical component in one package of the jelly composition include 600 to 900 mg of EPA-E and any one to three members selected from 5 to 20 mg of pravastatin, 5 to 20 mg of simvastatin, 20 to 60 mg of fluvastatin, 5 to 40 mg of atorvastatin, 1 to 4 mg of pitavastatin, 2.5 to 20 mg of rosuvastatin, 5 to 20 mg of ezetimibe, 2 to 12 mg of candesartan, 25 to 100 mg of losartan, 40 to 160 mg of valsartan, 5 to 40 mg of olmesartan, 2.5 to 10 mg of enalapril, 2.5 to 5 mg of amlodipine, 5 to 20 mg of cilnidipine, 10 to 40 mg of nifedipine, 0.5 to 8 mg of doxazosin, 0.2 to 0.9 mg of voglibose, 150 to 750 mg of metformin, 15 to 45 mg of pioglitazone, 2 to 8 mg of rosiglitazone, 10 to 30 mg of metiglinide, 90 to 360 mg of nateglinide, and 3 to 5 mg of donepezil. Examples of the more preferable combinations include a combination of 600 mg of EPA-E and 10 mg of pravastatin, a combination of 600 mg of EPA-E and 10 mg of simvastatin, a combination of 600 mg of EPA-E and 10 mg of cilnidipine, a combination of 600 mg of EPA-E and 12 mg of candesartan, a combination of 600 mg of EPA-E and 45 mg of pioglitazone, a combination of 600 mg of EPA-E and 3 mg of donepezil, a combination of 600 mg of EPA-E, 5 mg of atorvastatin, and 5 mg of amlodipine, and a combination of 900 mg of EPA-E, 10 mg of simvastatin, and 0.9 mg of voglibose.

Content of the second pharmaceutical component in the entire jelly composition is preferably in the range of 0.01 to 20% by weight, and more preferably 0.02 to 10% by weight, and this content may be adequately selected depending on the pharmaceutical component.

In the jelly composition of the present invention, the polyunsaturated fatty acid and the second pharmaceutical component are preferably incorporated such that, when the jelly composition is taken, the polyunsaturated fatty acid and the second pharmaceutical component in the jelly composition are rapidly released into and absorbed from the digestive tract to exert their pharmacological effects.

The emulsifier incorporated in the jelly composition of the present invention is not particularly limited as long as the merits of the present invention are retained. Exemplary emulsifiers include sucrose fatty acid ester, glycerin fatty acid ester, polyglycerin fatty acid ester, lecithin, polyoxyethylene polyoxypropylene glycol, sorbitan fatty acid ester, propylene glycol fatty acid ester, and a saturated fatty acid containing 12 to 22 carbon atoms. These emulsifiers may be used in a content of 0.01 to 20% by weight, preferably 0.05 to 10% by weight, and more preferably 0.1 to 5% by weight in relation to the total amount of the jelly composition.

Examples of the sucrose fatty acid ester include stearate esters having an HLB of 1 to 5. The most preferred is the one having an HLB of 2 (Surfhope SE PHARMA J-1802).

Examples of the lecithin include soybean lecithin.

The polyoxyethylene polyoxypropylene glycol is preferably the one having an average degree of polymerization of the propylene oxide of 5 and an average degree of polymerization of the ethylene oxide of 105 (PEP-101), or the one having an average degree of polymerization of the propylene oxide of 30 and an average degree of polymerization of the ethylene oxide of 160 (Pluronic F68). The most preferred is the one having an average degree of polymerization of the propylene oxide of 5 and an average degree of polymerization of the ethylene oxide of 105.

Exemplary sorbitan fatty acid esters include sorbitan monolaurate, sorbitan sesquioleate, sorbitan monostearate, and sorbitan monooleate, and the preferred is sorbitan monolaurate.

Exemplary propylene glycol fatty acid esters include propylene glycol dicaprylate, propylene glycol monocaprylate, and propylene glycol dicaprate, and the preferred is propylene glycol dicaprylate.

Examples of the saturated fatty acid containing 12 to 22 carbon atoms include stearic acid, myristic acid, and palmitic acid, and the preferred is stearic acid.

Incorporation of such emulsifier prevents oxidation of the polyunsaturated fatty acid in the jelly composition, and hence, the polyunsaturated fatty acid will be stable.

These emulsifiers may be used alone or in combination of two or more. When the emulsifier is used alone, use of polyoxyethylene polyoxypropylene glycol in a content of 0.1 to 10% by weight is preferable.

When a combination of two or more emulsifiers is used, the preferable combinations include polyoxyethylene polyoxypropylene glycol and at least one member selected from sucrose fatty acid ester, lecithin, sorbitan fatty acid ester, propylene glycol fatty acid ester, and a saturated fatty acid containing 12 to 22 carbon atoms. Each of these emulsifiers may be incorporated in an amount of 0.1 to 10% by weight.

One of the particularly preferable combinations of the emulsifiers is a combination of PEP-101 and Surfhope SE PHARMA J-1802.

Another example of the particularly preferable combination of the emulsifiers is PEP-101, Surfhope SE PHARMA J-1802, and stearic acid.

Still another example of the particularly preferable combination of the emulsifiers is Pluronic F68 and soybean lecithin.

Yet another example of the particularly preferable combination of the emulsifiers is PEP-101 and sorbitan monolaurate.

A further example of the particularly preferable combination of the emulsifiers is PEP-101 and propylene glycol dicaprylate.

Yet still another example of the particularly preferable combination of the emulsifiers is PEP-101, stearic acid, and propylene glycol dicaprylate.

The gelling agent incorporated in the jelly composition of the present invention is not particularly limited as long as the merits of the present invention are retained. Exemplary gelling agents include carageenan, sodium alginate, guar gum, locust bean gum, tara gum, xanthan gum, cellulose derivative, carboxyvinyl polymer, carmellose sodium, and pullulan, which may be incorporated in a total content of 0.01 to 20% by weight, and preferably 0.1 to 10% by weight. These gelling agents may be used alone or in combination of two or more. Preferably, the gelling agent is the one containing at least one member selected from carageenan, locust bean gum, carmellose sodium, and pullulan, which may be desirably incorporated in a content of 0.05 to 10% by weight. More preferably, the gelling agent is the one containing carageenan, locust bean gum, pullulan, and/or carmellose sodium, which may be desirably incorporated in a content of 0.05 to 10% by weight.

A preferable embodiment of the jelly composition according to the present invention is the one which has an adequate jelly strength that enables stable storage, high portability, and easy taking, and once taken, which disintegrates in the mouth or in the digestive tract so that the polyunsaturated fatty acid and the second pharmaceutical component are rapidly released in the digestive tract. Such action is realized by using the gelling agent of the present invention.

Increase in the releasability of the polyunsaturated fatty acid and the second pharmaceutical component can be realized in some cases by reducing the jelly strength to facilitate disintegration of the jelly. However, when the jelly strength is too low, the jelly can no longer be taken as a single mass, and some part of the jelly may be left in the container or spilled. In such a case, reliable administration of the predetermined amount of drug is no longer possible. On the contrary, the jelly having an excessively high jelly strength will not readily disintegrate in the mouse or in the digestive tract, and it will not form a mass with the saliva, and swallowing will be difficult and may become the cause of aspiration. Accordingly, a jelly having an adequate jelly strength is an example of the jelly which can be easily taken.

The jelly strength of the jelly composition in the present invention is indicated by the value (breaking strength) obtained by measuring the maximum stress (gf) on the plunger using the following apparatus under the following conditions, and dividing the measured maximum stress by the cross section of the plunger ($cm^2$).

Apparatus (rheometer) used: texture analyzer TA-XT-PLUS (manufactured by Stable Micro Systems Ltd.)

Inner diameter of the container used for filling the jelly composition: 20 mm

Plunger used: columnar shape with a diameter of 10 mm

Insertion speed: 30 cm/min

Insertion distance: 10 mm

Temperature: room temperature (about 25° C.)

In the present invention, the jelly having an adequate jelly strength (breaking strength) is the jelly having a jelly strength (breaking strength) of at least 50 $gf/cm^2$ and up to 250 $gf/cm^2$ when the jelly strength is measured by filling the jelly composition in a cylindrical container having an inner diameter of 20 mm by the apparatus as described above, and it is pushed with a columnar plunger having a diameter of 10 mm at an insertion speed of 30 cm/min to an insertion distance of 10 mm at room temperature. Such jelly exhibits excellent portability as well as ease of taking with adequate jelly strength so that it can be swallowed at once.

On the other hand, the jelly adapted for the administration to the so called "bedridden" patients from the tube is preferably a jelly which is easily dispersible in water, and the jelly strength is not particularly limited.

Exemplary combinations of the emulsifier and the gelling agent include combinations of the emulsifier containing at least one member selected from the group consisting of polyoxyethylene polyoxypropylene glycol, sucrose fatty acid ester, lecithin, sorbitan fatty acid ester, propylene glycol fatty acid ester, and a saturated fatty acid containing 12 to 22 carbon atoms and a gelling agent containing carageenan, locust bean gum, pullulan, and/or carmellose sodium. Preferable content of each component is 0.5 to 5% by weight for polyoxyethylene polyoxypropylene glycol, 0.1 to 3% by weight for sucrose fatty acid ester, 0.1 to 3% by weight for lecithin, 0.1 to 5% by weight for sorbitan fatty acid ester, 0.1 to 5% by weight for propylene glycol fatty acid ester, 0.1 to 5% by weight for a saturated fatty acid containing 12 to 22 carbon atoms, 0.1 to 2% by weight for carageenan, 0.05 to 1% by weight for locust bean gum, 0.5 to 5% by weight for pullulan, and 0.1 to 2% by weight for carmellose sodium.

In the present invention, a syneresis inhibitor is used to secure long term stability by suppressing syneresis of the jelly composition. Exemplary syneresis inhibitors include carmellose sodium, pullulan, poly(sodium acrylate), hydroxypropyl methylcellulose, hydroxypropyl cellulose, and crystalline cellulose. The syneresis inhibitor is preferably incorporated in an amount of 0.01 to 10% by weight, and more preferably in 0.05 to 5% by weight. A content lower than such range is insufficient to show the effect of suppressing the syneresis, whereas a content in excess of such range may invite excessive increase in the viscosity during the preparation rendering production of the homogeneous solution difficult. Such syneresis inhibitor may be used alone or in combination of two or more. The preferred are carmellose sodium and/or pullulan.

In the present invention, a gelling aid may be added in order to suppress increase in the viscosity of the emulsion containing the polyunsaturated fatty acid during the preparation stage, for ease of filling in the container, and simultaneously, to improve jelly strength of the cooled jelly composition. More specifically, the gelling aid used may be calcium lactate, potassium chloride, or the like, and the preferred is calcium lactate. When a gelling aid is added, it may be incorporated in a content of 0.01 to 10% by weight, and preferably 0.1 to 2% by weight.

The jelly composition of the present invention may also contain a corrigent (for example, sorbitol, erythritol, maltitol, mannitol, xylitol, or trehalose), a flavoring agent (for example, orange oil, peppermint oil, or apple flavor), a preservatibe (for example, sodium citrate, methyl paraoxybenzoate, or propyl paraoxybenzoate), an antioxidant (for example, tocopherol, tocopherol acetate, propyl gallate, ascorbyl stearate, glycine, sodium ascorbate, or sodium erythorbate), an emulsifier aid (for example, conc. glycerin or macrogol), a pH adjusting agent (for example, citric acid, acetic acid, phosphoric acid, sodium hydrogencarbonate, or sodium hydroxide), a buffer, a colorant, and an antifoaming agent (for example, silicone oil). These additives are not particularly limited, as long as they are commonly used in pharmaceutical products or food. Also, they may be used in combination of two or more. Exemplary preferable corrigents include sorbitol, erythritol, xylitol, and trehalose, which may be incorporated in 3 to 30% by weight. Exemplary flavoring agents include oily flavors, and in particular, orange oil, which may be incorporated in an amount of 0.01 to 3% by weight. Preferred emulsifier aid is conc. glycerin, which may be incorporated in an amount of 2 to 20% by weight.

The jelly composition of the present invention may be prepared by a method commonly used in the art in preparing a jelly composition as long as the merits of the present invention are retained. More specifically, the jelly composition may be prepared by mixing the polyunsaturated fatty acid, the second pharmaceutical component, the emulsifier, the gelling agent, purified water, and other components in arbitrary order, and homogenizing to allow the mixture to gelate.

Next, an embodiment of a process of preparing the jelly composition of the present invention is described, which by no means limits the scope of the present invention. The polyunsaturated fatty acid and the emulsifier are thoroughly mixed with a small amount of water and the emulsifier aid, and the mixture is homogeneously mixed in an agitator. This mixture is heated, and a predetermined amount of water is added in small portions for emulsification. Next, powder or granular bulk, triturated powder or granule, pulverized commercially available tablet or content of the commercially available capsule, solution, suspension, emulsion, or the like of the second pharmaceutical component is added, and the mixture is homogeneously mixed by using an agitator. Next, the gelling agent is added optionally with the gelling aid, and the mixture is heated and vigorously agitated for homogenization. A dose of this solution is filled in an appropriate container, and the jelly is formed by cooling. The container of the jelly composition is not particularly limited for its shape as long as the jelly composition can be filled, and the thus filled jelly composition can be readily administered. Exemplary containers include cup-shaped or tubular containers. In view of the production, portability, and ease of taking, the preferred is an elongated container formed from a heat sealable laminate film. A more preferable embodiment of the container is an elongated container having a gas filled at an end so that the jelly composition can be pushed out of the container at once by cutting an end of the laminate film and pushing the gas from both sides. Since the polyunsaturated fatty acid is susceptible to oxidization during the production, use of a container with low oxygen permeability or further wrapping of the container with a material having low oxygen permeability is preferable. Amount of the jelly composition filled in one container is preferably in the range of 0.5 to 10 g, and more preferably 1 to 6 g.

An embodiment of the present invention is the jelly composition which has been individually packaged by the process as described above so that one dose of the jelly composition is retained in one container.

Since the polyunsaturated fatty acid is susceptible to oxidation during the production, at least a part of the production process is preferably conducted in nitrogen atmosphere, and it is more preferable to conduct all production process in nitrogen atmosphere. By conducting the production under such fully controlled conditions, peroxide value (POV) of the polyunsaturated fatty acid immediately after the production of the jelly composition can be reduced to the level of up to 10 meq/kg. Since quality of the polyunsaturated fatty acid is easily lost by oxidation and peculiar taste and smell develops with such loss of the quality, prevention of the deterioration of the polyunsaturated fatty acid and control of the POV of the polyunsaturated fatty acid in the jelly composition to the level of up to 10 meq/kg during the production is important in producing the jelly composition which can be easily taken. When a degassed water or deoxygenated water is used for the water used in the production of the jelly composition of the present invention, POV of the polyunsaturated fatty acid in the jelly composition can be maintained at a low level, which is advantageous.

The jelly composition of the present invention is well adapted for use as food, health food, food with health claims (food with nutrient function claims and food for specified health use), pharmaceutical preparation, and the like, and more specifically, as an orally administered pharmaceutical preparation. The jelly composition of the present invention is particularly suitable for use in a patient with less ability of swallowing or a patient who is allowed to take only limited amount of water.

The jelly composition of the present invention can be taken once to several times a day at any timing such as just after getting up, before, during, after, or between meals, or before going to bed as food, health food, food with health claims, pharmaceutical preparation, or the like.

A combination of a jelly composition not containing the second pharmaceutical component and the jelly composition of the present invention, or a combination of different jelly compositions of the present invention each having different formulation may be prepared as a set that can be taken or administered in one day. In this case, the corrigent and the flavoring agent, shape of the jelly composition, package design and the like can be adequately changed for each jelly composition.

In the present invention, the term "metabolic syndrome" designates a complication of a series of pathological conditions including obesity, hyperlipidemia, hypertension, and diabetes. Related concepts such as syndrome X, insulin resistance syndrome, visceral fat syndrome, and multiple risk factor syndrome are also included in the "metabolic syndrome" as used in the present invention. In the present invention, prevention of the metabolic syndrome means prevention or delaying of occurrence of the symptoms in at least two pathological conditions selected from the group of the pathological conditions as mentioned above. Similarly, in the present invention, treatment of the metabolic syndrome means amelioration or healing of the symptoms in at least two pathological conditions selected from the group of the pathological conditions as mentioned above.

Next, the present invention is described in further detail by referring to the Examples which by no means limit the scope of the present invention.

EXAMPLES

Example 1

Components of "A" in Table 1 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and after dissolution, the solution is filled in an elongated pouch of a laminate film at about 3 g/pouch. After heat sealing, it is cooled to prepare a jelly composition containing about 600 mg of ethyl icosapentate and about 10 mg of pravastatin.
[Table 1]

TABLE 1

| | Example 1 | |
|---|---|---|
| | Components | Content (% by weight) |
| A | Polyoxyethylene (105) polyoxypropylene (5) glycol | 1.13 |
| | Sucrose fatty acid ester | 0.47 |
| | Stearic acid | 1.00 |
| | Conc. glycerin | 7.50 |
| | Ascorbyl stearate | 0.02 |
| | Sodium erythorbate | 1.30 |
| | Orange oil | 0.90 |
| | Purified water | 15.00 |

TABLE 1-continued

| | Example 1 | |
|---|---|---|
| | Components | Content (% by weight) |
| B | Ethyl icosapentate | 20.00 |
| | Pravastatin | 0.33 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 2

A tablet containing 10 mg of cilnidipine (Atelec Tablets 10 manufactured by Ajinomoto Co., Inc. containing 10 mg of cilnidipine in a tablet of about 0.27 g) is pulverized by using a commercially available pulverizer, and a powder containing homogeneously dispersed cilnidipine is preliminarily prepared. Using this powder, the procedure of Example 1 is repeated for the components of Table 2 to prepare a jelly composition containing about 600 mg of ethyl icosapentate and about mg of cilnidipine.
[Table 2]

TABLE 2

| | Example 2 | |
|---|---|---|
| | Components | Content (% by weight) |
| A | Polyoxyethylene (105) polyoxypropylene (5) glycol | 1.00 |
| | Sorbitan monolaurate | 1.00 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 20.00 |
| | Cilnidipine | 0.33 (in terms of cilnidipine bulk) |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 3

The procedure of Example 1 is repeated for the components of Table 3 to prepare a jelly composition containing about 600 mg of ethyl icosapentate and about 12 mg of candesartan.
[Table 3]

TABLE 3

| | Example 3 | |
|---|---|---|
| | Components | Content (% by weight) |
| A | Polyoxyethylene (105) polyoxypropylene (5) glycol | 1.53 |

TABLE 3-continued

Example 3

| | Components | Content (% by weight) |
|---|---|---|
| | Propylene glycol dicaprylate | 0.87 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 20.00 |
| | Candesartan | 0.40 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 4

The procedure of Example 1 is repeated for the components of Table 4 to prepare a jelly composition containing about 600 mg of ethyl icosapentate and about 45 mg of pioglitazone.

[Table 4]

TABLE 4

Example 4

| | Components | Content (% by weight) |
|---|---|---|
| A | Polyoxyethylene (105) polyoxypropylene (5) glycol | 1.60 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 20.00 |
| | Pioglitazone | 1.5 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 5

Components of "A" in Table 5 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and after dissolution, components of "D" are added. Using this solution, the procedure of Example 1 is repeated to prepare a jelly composition containing about 600 mg of ethyl icosapentate and about 3 mg of donepezil.

[Table 5]

TABLE 5

Example 5

| | Components | Content (% by weight) |
|---|---|---|
| A | Polyoxyethylene (160) polyoxypropylene (30) glycol | 2.02 |
| | Soybean lecithin | 0.38 |
| | Conc. glycerin | 10.00 |
| | Purified water | 15.00 |
| B | Ethyl icosapentate | 20.00 |
| | Donepezil | 0.10 |
| | Purified water | 41.45 |
| C | Xylitol | 10.00 |
| | Carageenan | 0.45 |
| | Locust bean gum | 0.20 |
| D | Calcium lactate | 0.50 |

Example 6

The procedure of Example 1 is repeated for the components of Table 6 to prepare a jelly composition containing about 600 mg of ethyl icosapentate, about 5 mg of atorvastatin, and about 5 mg of amlodipine.

[Table 6]

TABLE 6

Example 6

| | Components | Content (% by weight) |
|---|---|---|
| A | Polyoxyethylene (105) polyoxypropylene (5) glycol | 1.53 |
| | Propylene glycol dicaprylate | 0.87 |
| | Stearic acid | 0.50 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 20.00 |
| | Atorvastatin | 0.17 |
| | Amlodipine | 0.17 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 7

The procedure of Example 1 is repeated for the components of Table 7 to prepare a jelly composition containing about 900 mg of ethyl icosapentate, about 10 mg of simvastatin, and about 0.9 mg of voglibose.

[Table 7]

TABLE 7

Example 7

| | Components | Content (% by weight) |
|---|---|---|
| A | Polyoxyethylene (105) polyoxypropylene (5) glycol | 2.02 |

TABLE 7-continued

Example 7

| | Components | Content (% by weight) |
|---|---|---|
| | Sucrose fatty acid ester | 0.84 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 30.00 |
| | Simvastatin | 0.33 |
| | Voglibose | 0.03 |
| | Sodium hydroxide | q.s. |
| | Purified water | q.s. |
| C | Trehalose | 7.50 |
| | Carageenan | 0.49 |
| | Locust bean gum | 0.25 |
| | Pullulan | 1.50 |

Test Example 1

In the test in which the jelly compositions of Examples 1 to 7 are left to stand at a temperature of 40° C. and a relative humidity of 75% for 6 months, and are then evaluated for their change in the outer appearance (shape, occurrence of syneresis, and the like), the jelly compositions of Examples 1 to 7 exhibit no change in the shape or occurrence of syneresis.

Test Example 2

In the case where the jelly compositions of Examples 1 to 7 are tested by a method based on the paddle method defined for the dissolution test in the Japanese Pharmacopeia (International Journal of Pharmaceutics, vol. 95, pp. 67 to 75) which involves introducing 160 mL of an artificial gastric juice (an aqueous solution containing 115 mmol/L of sodium chloride and 35 mmol/L of potassium chloride which had been adjusted with hydrochloric acid to a pH of 2.5) serving as a test solution as well as 2000 nylon beads (diameter, 6.4 mm) in a beaker for use in a dissolution tester and stirring at a temperature of 37° C. and a paddle rotation rate of 25 to evaluate the release of the ethyl icosapentate and the second pharmaceutical component into the test solution, the jelly compositions of Examples 1 to 7 exhibit excellent release.

Test Example 3

In the test of measuring the concentrations in plasma of the EPA and the second pharmaceutical component by orally administering the jelly compositions of Examples 1 to 6 in an amount of 900 mg in terms of the ethyl icosapentate to each group of beagles after having been fed on softened feed, the jelly compositions of Examples 1 to 6 exhibit excellent increases of the blood concentrations for both the EPA and the second pharmaceutical component.

Test Example 4

In the test in which 1 g each of the jelly compositions of Examples 1 to 7 is homogeneously dispersed in the sodium phosphate buffer, chloroform is added to the dispersion to extract the ethyl icosapentate, and the peroxide value (POV) of the polyunsaturated fatty acid in the jelly composition is determined by the standard testing method for oils and fats (JAPAN Oil Chemists' Society), the jelly compositions of Examples 1 to 7 have POV values of up to 5 meq/kg.

Test Example 5

The value (breaking strength) is obtained by measuring the maximum stress (gf) on the plunger using the following apparatus under the following conditions, and dividing the measured maximum stress by the cross section of the plunger ($cm^2$).

Apparatus (rheometer) used: texture analyzer TA-XT-PLUS (manufactured by Stable Micro Systems Ltd.)

Inner diameter of the container used for filling the jelly composition: 20 mm

Plunger used: columnar shape with a diameter of 10 mm

Insertion speed: 30 cm/min

Insertion distance: 10 mm

Temperature: room temperature (about 25° C.)

The jelly compositions of Examples 1 to 7 have a jelly strength of 10 to 250 $gf/cm^2$.

Reference Example 1

Components of "A" in Table 8 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and the preparation obtained after homogenization is filled in an elongated pouch of a laminate film at about 3 g/pouch. After heat sealing, it is cooled to prepare a jelly composition containing about 600 mg of ethyl icosapentate.

[Table 8]

TABLE 8

| | Components | Content (% by weight) |
|---|---|---|
| A | Polyoxyethylene (105) polyoxypropylene (5) glycol | 1.13 |
| | Sucrose fatty acid ester | 0.47 |
| | Stearic acid | 1.00 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 20.00 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 8

Components of "A" in Table 9 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and the preparation obtained after homogenization is filled in an elongated pouch of a laminate film at about 3 g/pouch. After heat sealing, it is cooled to prepare a jelly composition containing about 600 mg of ethyl icosapentate and about 10 mg of pravastatin sodium.

[Table 9]

TABLE 9

| | Components | Content (% by weight) |
|---|---|---|
| A | Polyoxyethylene (105) polyoxypropylene (5) glycol | 1.13 |
| | Sucrose fatty acid ester | 0.47 |
| | Stearic acid | 1.00 |
| | Conc. glycerin | 7.50 |
| | Ascorbyl stearate | 0.02 |
| | Sodium erythorbate | 1.30 |
| | Orange oil | 0.90 |
| | Pravastatin sodium | 0.33 |
| | Purified water | 15.00 |
| B | Ethyl icosapentate | 20.00 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 9

Components of "A" in Table 10 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and the preparation obtained after homogenization is filled in an elongated pouch of a laminate film at about 3 g/pouch. After heat sealing, it is cooled to prepare a jelly composition containing about 600 mg of ethyl icosapentate and about 10 mg of simvastatin.

[Table 10]

TABLE 10

| | Components | Content (% by weight) |
|---|---|---|
| A | Polyoxyethylene (105) polyoxypropylene (5) glycol | 1.13 |
| | Sucrose fatty acid ester | 0.47 |
| | Stearic acid | 1.00 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 20.00 |
| | Simvastatin | 0.33 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Test Example 6

The jelly compositions of Reference Example 1 and Examples 8 and 9 are observed for their appearance and the pH is also measured. These compositions are also evaluated for their jelly strength by the procedure as described above. As an example, the results are shown in Table 11. The jelly compositions of Examples 8 and 9 containing the second pharmaceutical component had substantially the same appearance and pH as those of the jelly composition of Reference Example 1 not containing the second pharmaceutical component, as well as a jelly strength in the range of 50 to 250 gf/cm$^2$ which is appropriate for use as a pharmaceutical product.

[Table 11]

TABLE 11

| | Appearance | pH | Jelly strength (gf/cm$^2$) |
|---|---|---|---|
| Reference Example 1 | Slightly yellowish white jelly | 5.56 | 183 |
| Example 8 | Slightly yellowish white jelly | 5.58 | 148 |
| Example 9 | Slightly yellowish white jelly | 5.63 | 129 |

Reference Example 2

Components of "A" in Table 12 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and the preparation obtained after homogenization is filled in an elongated pouch of a laminate film at about 3 g/pouch. After heat sealing, it is cooled to prepare a jelly composition containing about 600 mg of ethyl icosapentate.

[Table 12]

TABLE 12

| | Components | Content (% by weight) |
|---|---|---|
| A | Polyoxyethylene (105) polyoxypropylene (5) glycol | 1.00 |
| | Sorbitan monolaurate | 1.00 |
| | Conc. glycerin | 7.50 |
| | Ascorbyl stearate | 0.02 |
| | Sodium erythorbate | 1.30 |
| | Orange oil | 0.90 |
| | Purified water | 15.00 |
| B | Ethyl icosapentate | 20.00 |
| | Sodium hydroxide | q.s. |
| | Purified water | q.s. |
| C | Trehalose | 15.00 |
| | Carageenan | 0.42 |
| | Locust bean gum | 0.25 |
| | Pullulan | 3.00 |

Example 10

Components of "A" in Table 13 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and the preparation obtained after homogenization is filled in an elongated pouch of a laminate film at about 3 g/pouch. After heat sealing, it is cooled to prepare a jelly composition containing about 600 mg of ethyl icosapentate and about 10 mg of pravastatin sodium.

[Table 13]

TABLE 13

|   | Components | Content (% by weight) |
|---|---|---|
| A | Polyoxyethylene (105) polyoxypropylene (5) glycol | 1.00 |
|   | Sorbitan monolaurate | 1.00 |
|   | Conc. glycerin | 7.50 |
|   | Ascorbyl stearate | 0.02 |
|   | Sodium erythorbate | 1.30 |
|   | Orange oil | 0.90 |
|   | Pravastatin sodium | 0.33 |
|   | Purified water | 15.00 |
| B | Ethyl icosapentate | 20.00 |
|   | Sodium hydroxide | q.s. |
|   | Purified water | q.s. |
| C | Trehalose | 15.00 |
|   | Carageenan | 0.42 |
|   | Locust bean gum | 0.25 |
|   | Pullulan | 3.00 |

Example 11

Components of "A" in Table 14 are weighed, mixed, and heated to 80° C. for dissolution in nitrogen atmosphere (oxygen concentration, up to 0.2%). To this mixture are added components of "B", and the mixture is emulsified by high speed agitation. Components of "C" are then added, and the preparation obtained after homogenization is filled in an elongated pouch of a laminate film at about 3 g/pouch. After heat sealing, it is cooled to prepare a jelly composition containing about 600 mg of ethyl icosapentate and about 10 mg of simvastatin.

[Table 14]

TABLE 14

|   | Components | Content (% by weight) |
|---|---|---|
| A | Polyoxyethylene (105) polyoxypropylene (5) glycol | 1.00 |
|   | Sorbitan monolaurate | 1.00 |
|   | Conc. glycerin | 7.50 |
|   | Ascorbyl stearate | 0.02 |
|   | Sodium erythorbate | 1.30 |
|   | Orange oil | 0.90 |
|   | Purified water | 15.00 |
| B | Ethyl icosapentate | 20.00 |
|   | Simvastatin | 0.33 |
|   | Sodium hydroxide | q.s. |
|   | Purified water | q.s. |
| C | Trehalose | 15.00 |
|   | Carageenan | 0.42 |
|   | Locust bean gum | 0.25 |
|   | Pullulan | 3.00 |

Test Example 7

The jelly compositions of Reference Example 2 and Examples 10 and 11 are observed for their appearance and the pH is also measured. These compositions are also evaluated for their jelly strength by the procedure as described above. As an example, the results are shown in Table 15. The jelly compositions of Examples 10 and 11 containing the second pharmaceutical component had substantially the same appearance and pH as those of the jelly composition of Reference Example 2 not containing the second pharmaceutical component, as well as a jelly strength in the range of 50 to 250 gf/cm² which is appropriate for use as a pharmaceutical product.

[Table 15]

TABLE 15

|   | Appearance | pH | Jelly strength (gf/cm²) |
|---|---|---|---|
| Reference Example 2 | Slightly yellowish white jelly | 7.29 | 186 |
| Example 10 | Slightly yellowish white jelly | 7.37 | 179 |
| Example 11 | Slightly yellowish white jelly | 7.07 | 188 |

Test Example 8

In order to compare the release of the ethyl icosapentate into a test solution, the jelly compositions of Reference Example 2 and Examples 10 and 11 are tested by a method based on the paddle method defined for the dissolution test in the Japanese Pharmacopeia (International Journal of Pharmaceutics, vol. 95, pp. 67 to 75) which involves introducing 160 mL of an artificial gastric juice (an aqueous solution containing 115 mmol/L of sodium chloride and 35 mmol/L of potassium chloride which had been adjusted with hydrochloric acid to a pH of 2.5) serving as the test solution as well as 2000 nylon beads (diameter, 6.4 mm) in a beaker for use in a dissolution tester and stirring at a temperature of 37° C. and a paddle rotation rate of 25. As an example, the test results are shown in Table 16. Any of the jelly compositions of Examples 10 and 11 having the second pharmaceutical component added thereto had a release ratio at 30 minutes of higher than 50% and exhibited good release.

[Table 16]

TABLE 16

|   | Release ratio at 30 minutes (%) |
|---|---|
| Reference Example 2 | 92.1 |
| Example 10 | 57.4 |
| Example 11 | 59.4 |

The invention claimed is:

1. A pharmaceutical jelly composition formulated for oral administration, said pharmaceutical jelly composition comprising:
    a first pharmaceutical component comprising icosapentaenoic acid or an ethyl ester thereof;
    a second pharmaceutical component comprising an antihyperlipidemic agent selected from the group consisting of statin drugs (HMG-CoA reductase inhibitors), fibrates, squalene synthase inhibitor, and cholesterol absorption inhibitor;
    from 0.05 to 10% by weight, based upon the total weight of the jelly composition, of an emulsifying agent which is at least one member selected from the group consisting of polyoxyethylene polyoxypropylene glycol, sucrose fatty acid ester, lecithin, polyglycerin fatty acid ester, glycerin fatty acid ester, sorbitan fatty acid ester, propylene glycol fatty acid ester, and a saturated fatty acid containing 12 to 22 carbon atoms;
    a gelling agent which is at least one member selected from the group consisting of carrageenan and locust bean gum; and from 0.5 to 5% by weight, based upon the total weight of the jelly composition, of a syneresis inhibitor selected from the group consisting of carmellose sodium, pullulan, hydroxypropyl methylcellulose, hydroxypropyl cellulose, and crystalline cellulose, wherein said pharmaceutical jelly composition has a jelly strength of 50 to 250gf/cm$^2$ and wherein said pharmaceutical jelly composition has a release ratio of higher than 50% of icosapentaenoic acid or an ethyl ester thereof, into a test solution in a beaker containing 2000nylon beads having a diameter of 6.4 mm, 30 minutes after mixing the jelly composition into the test solution and stirring at a temperature of 37° C. with a paddle rotation rate of 25, said test solution being composed of 160 mL of an artificial gastric juice comprising an aqueous solution containing 115 mmol/L of sodium chloride and 35 mmol/L of potassium chloride adjusted with hydrochloric acid to a pH of 2.5.

2. The jelly composition according to claim 1, wherein the jelly composition further comprises at least one member selected from the group consisting of corrigent, flavoring agent, preservative, antioxidant, gelling aid, emulsifier aid, and pH adjusting agent.

3. The jelly composition according to claim 1 wherein the composition has been divided into single doses.

4. The jelly composition according to claim 1, wherein
the icosapentaenoic acid or an ethyl ester thereof constitutes 10 to 50% by weight,
the second pharmaceutical component constitutes 0.01 to 20% by weight,
the emulsifier constitutes 0.1 to 5% by weight, and
the gelling agent constitutes 0.01 to 20% by weight
of the entire jelly composition.

5. The jelly composition according to claim 1 wherein the composition is a therapeutic agent for metabolic syndrome.

6. The jelly composition according to claim 1, wherein the emulsifier is a polyoxyethylene polyoxypropylene glycol.

7. The jelly composition according to claim 4, wherein the emulsifier is a polyoxyethylene polyoxypropylene glycol.

8. The jelly composition according to claim 1, wherein the antihyperlipidemic agent is selected from the group consisting of pravastatin, simvastatin, lovastatin, fluvastatin, atorvastatin, cerivastatin, pitavastatin, rosuvastatin, bezafibrate, fenofibrate, lapaquistat, and ezetimibe.

* * * * *